US011833496B2

(12) United States Patent
Ou

(10) Patent No.: US 11,833,496 B2
(45) Date of Patent: *Dec. 5, 2023

(54) RAPID CURE SILICONE LUBRICIOUS COATINGS

(71) Applicant: Ethicon, Inc., Somerville, NJ (US)

(72) Inventor: Duan Li Ou, Watchung, NJ (US)

(73) Assignee: Ethicon, Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/553,237

(22) Filed: Dec. 16, 2021

(65) Prior Publication Data

US 2022/0105502 A1 Apr. 7, 2022

Related U.S. Application Data

(60) Division of application No. 16/052,856, filed on Aug. 2, 2018, now Pat. No. 11,224,869, which is a continuation of application No. 15/272,538, filed on Sep. 22, 2016, now abandoned, which is a division of application No. 15/232,085, filed on Aug. 9, 2016, now Pat. No. 10,441,947, which is a division of application No. 13/296,771, filed on Nov. 15, 2011, now Pat. No. 9,434,857.

(51) Int. Cl.

| | | |
|---|---|---|
| *B01J 31/00* | (2006.01) | |
| *B01J 31/22* | (2006.01) | |
| *A61L 29/08* | (2006.01) | |
| *A61L 31/10* | (2006.01) | |
| *A61L 29/14* | (2006.01) | |
| *A61L 31/14* | (2006.01) | |
| *C09D 183/04* | (2006.01) | |
| *C10M 107/50* | (2006.01) | |
| *C10M 139/06* | (2006.01) | |
| *B01J 31/16* | (2006.01) | |
| *C08G 77/12* | (2006.01) | |
| *C08G 77/20* | (2006.01) | |
| *C08L 83/00* | (2006.01) | |
| *B05D 5/08* | (2006.01) | |
| *C10N 40/00* | (2006.01) | |
| *C10N 50/00* | (2006.01) | |

(52) U.S. Cl.
CPC ......... *B01J 31/2282* (2013.01); *A61L 29/085* (2013.01); *A61L 29/14* (2013.01); *A61L 31/10* (2013.01); *A61L 31/14* (2013.01); *B01J 31/1608* (2013.01); *C09D 183/04* (2013.01); *C10M 107/50* (2013.01); *C10M 139/06* (2013.01); *A61L 2400/10* (2013.01); *A61L 2420/04* (2013.01); *B05D 5/08* (2013.01); *C08G 77/12* (2013.01); *C08G 77/20* (2013.01); *C08L 83/00* (2013.01); *C10M 2227/08* (2013.01); *C10M 2229/0415* (2013.01); *C10M 2229/0445* (2013.01); *C10N* *2040/50* (2020.05); *C10N 2050/015* (2020.05); *Y10T 428/31612* (2015.04); *Y10T 428/31663* (2015.04)

(58) Field of Classification Search
None
See application file for complete search history.

(56) References Cited

U.S. PATENT DOCUMENTS

| | | | |
|---|---|---|---|
| 3,775,452 A | 11/1973 | Karstedt | |
| 3,814,730 A | 6/1974 | Karstedt | |
| 4,500,688 A | 2/1985 | Arkles | |
| 4,720,521 A | 1/1988 | Spielvogel et al. | |
| 4,806,430 A | 2/1989 | Spielvogel et al. | |
| 4,838,876 A | 6/1989 | Wong et al. | |
| 4,987,169 A | 1/1991 | Kuwata et al. | |
| 5,026,607 A | 6/1991 | Kiezulas | |
| 5,084,315 A | 1/1992 | Karimi et al. | |
| 5,494,750 A * | 2/1996 | Fujioka | C08L 83/04 428/407 |
| 5,536,582 A | 7/1996 | Prasad et al. | |
| 5,776,268 A | 7/1998 | Mcjames et al. | |
| 5,911,711 A | 6/1999 | Pelkey | |
| 5,977,249 A * | 11/1999 | Kovar | C08K 5/36 524/742 |
| 6,015,398 A | 1/2000 | Arimatsu et al. | |
| 6,093,782 A | 7/2000 | Herzig et al. | |

(Continued)

FOREIGN PATENT DOCUMENTS

| | | |
|---|---|---|
| CN | 101528281 | 3/2014 |
| EP | 2554205 A1 | 2/2013 |

(Continued)

OTHER PUBLICATIONS

Canty, et al., n1-Alkynyl Chemistry for the Higher Oxidation States of Palladium and Platinum, Higher Oxidation State Organopaliadium and Platinum Chemistry Topics in Organametalic Chemistry, 2011, pp. 111-127, vol. 35.
Ryan, et al ., Ultra-high-molecular-weight functional siloxane additives in polymers. Effects on processing and properties, Journal of Vinyl and Additive Technology, 2000, pp. 7-19, vol. 6 issue 1.
Ryan, et al., Ultra High Molecular Weight Functional Siloxane Additives in Polymers: Effects on Processing and Properties, Dow Corning Corporation, 1999, pp. 1-16, Page Number.
Silicone Solutions for Lubrication in Medical Application, Techbriefs Media Grou, retrieved from the internet Jan. 2010, 4 pages.

(Continued)

*Primary Examiner* — Stefanie J Cohen
(74) *Attorney, Agent, or Firm* — David R. Crichton; Leo Kriksunov

(57) ABSTRACT

Novel, lubricious coatings for medical devices are disclosed. The coatings provide improved lubricity and durability, and are readily applied in coating processes. The present invention is also directed to a novel platinum catalyst for use in such coatings. The catalyst provides for rapid curing, while inhibiting cross-linking at ambient temperatures, thereby improving the production pot life of the coatings.

2 Claims, No Drawings

(56) References Cited

U.S. PATENT DOCUMENTS

| | | | |
|---|---|---|---|
| 6,491,980 B1* | 12/2002 | Muller | C09D 183/04 |
| | | | 428/447 |
| 6,518,371 B1 | 2/2003 | Fink et al. | |
| 6,656,167 B2 | 12/2003 | Numao et al. | |
| 6,936,297 B2 | 8/2005 | Roby et al. | |
| 7,332,227 B2 | 2/2008 | Hardman et al. | |
| 7,354,628 B2 | 4/2008 | Steube | |
| 9,434,857 B2* | 9/2016 | Ou | B01J 31/2282 |
| 10,441,947 B2* | 10/2019 | Ou | C10M 107/50 |
| 11,224,869 B2* | 1/2022 | Ou | C09D 183/04 |
| 2001/0018491 A1* | 8/2001 | Shiono | C09J 183/08 |
| | | | 525/100 |
| 2002/0132071 A1 | 9/2002 | Buongiorno | |
| 2002/0132902 A1* | 9/2002 | Shiono | C08G 65/336 |
| | | | 524/492 |
| 2003/0114882 A1 | 6/2003 | Roby | |
| 2003/0171777 A1 | 9/2003 | Roby et al. | |
| 2003/0236552 A1 | 12/2003 | Roby | |
| 2004/0209784 A1 | 10/2004 | Hardman et al. | |
| 2004/0219449 A1 | 11/2004 | Landa et al. | |
| 2005/0038277 A1 | 2/2005 | Blanc-magnard et al. | |
| 2005/0203201 A1 | 9/2005 | Steube | |
| 2006/0128921 A1 | 6/2006 | Cray et al. | |
| 2006/0190040 A1 | 8/2006 | Roby | |
| 2007/0009748 A1 | 1/2007 | Takanami | |
| 2007/0020468 A1 | 1/2007 | Ekeland et al. | |
| 2007/0078236 A1 | 4/2007 | Bonnet et al. | |
| 2007/0228669 A1 | 10/2007 | Liu et al. | |
| 2008/0071228 A1 | 3/2008 | Wu et al. | |
| 2009/0264912 A1 | 10/2009 | Nawrocki et al. | |
| 2011/0046310 A1 | 2/2011 | Kashiwagi et al. | |
| 2011/0112565 A1 | 5/2011 | Maurer et al. | |
| 2011/0152926 A1 | 6/2011 | Vetrecin | |
| 2011/0248312 A1 | 10/2011 | Katayama | |
| 2013/0030380 A1 | 1/2013 | Abe et al. | |
| 2013/0195778 A1 | 8/2013 | Chodorowski-kimmes et al. | |

FOREIGN PATENT DOCUMENTS

| | | |
|---|---|---|
| JP | 07-026147 | 1/1995 |
| JP | 03064361 B2 | 7/2000 |
| JP | 2008193433 A | 8/2008 |
| JP | 2009532530 A | 9/2009 |
| JP | 2011132524 A | 7/2011 |
| JP | 2011219597 A | 11/2011 |
| RU | 2138528 C1 | 9/1999 |
| WO | 2004/009146 A1 | 1/2004 |
| WO | 2011056453 A1 | 5/2011 |
| WO | 2011122574 A1 | 10/2011 |

OTHER PUBLICATIONS

American Chemical Society (ACS) Scifinder Registry No. 42557-10-8 (2013).

International Preliminary Report re: PCT/US2012/065182; dated May 30, 2014.

International Search Report re: PCT/US2012/065182; dated Feb. 21, 2013.

Written Opinion re: PCT/US2012/065182; dated Feb. 25, 2013.

* cited by examiner

RAPID CURE SILICONE LUBRICIOUS COATINGS

This application is a divisional application of U.S. application Ser. No. 16/052,856 filed Aug. 2, 2018, now U.S. Pat. No. 11,224,869, which is a continuation of co-pending U.S. application Ser. No. 15/272,538 filed on Sep. 22, 2016, now abandoned, which is a divisional of U.S. application Ser. No. 15/232,085 filed on Aug. 9, 2016, now U.S. Pat. No. 10,441,947 issued on Oct. 15, 2019, which is a divisional of U.S. application Ser. No. 13/296,771 filed on Nov. 15, 2011, now U.S. Pat. No. 9,434,857 issued on Sep. 6, 2016; the entire disclosures of which are hereby incorporated herein by reference for all purposes.

TECHNICAL FIELD

The field of art to which this invention pertains is silicone-based lubricious coatings, in particular, silicone-based lubricious coatings for use on medical devices.

BACKGROUND OF THE INVENTION

Lubricious coatings are typically required for implantable or insertable medical devices such as hypodermic needles, surgical needles, catheters, and cutting devices that contact tissue. The primary purpose of such coatings is to ease the penetration or insertion of the device into and through tissue, thereby facilitating a procedure.

A number of conventional, biocompatible lubricants have been developed for such applications, and they are typically silicone (e.g., polydimethylsiloxane) or silicone-containing coatings. For example, condensation-cured silicone coatings are known to be useful as lubricious coatings on medical devices. Such coating formulations contain amino and alkoxyl functional groups, which can be cured (cross-linked) at relatively low temperatures and high humidity levels. It is also known to use an aminopropyl-containing silicone as a lubricious coating for syringe needles. Those coatings use an epoxy-containing silicone as a cross-linking agent and may have improved penetration performance with multiple penetrations. It is also known to utilize thermoplastic polymers such as polypropylene (e.g., in powder form) in blends of silicone solutions to improve the mechanical properties of the resulting coating layers. The polypropylene powders may increase the durability of silicone needle coatings without sacrificing lubricity. Most of the known and conventionally used silicone coatings listed above require a lengthy thermal curing step after application, which is quite often unsuitable for rapid, high speed production processes.

Attempts have been made to improve coating cure times including rapid UV curable silicone lubricious coatings that can be cured rapidly (<10 seconds) on a medical device, such as needle, after UV light exposure. However, the potential hazard of certain UV curable components typically contained in such coatings may provide cause for concern.

Karstedt of GE Silicone invented a highly active platinum catalyst for hydrosilylation at the beginning of the 1970's (U.S. Pat. No. 3,775,452). The "Karstedt catalyst" is highly active at ambient temperature, and this quality makes it difficult to use in most commercial silicone coatings without the addition of an inhibitor. Several other platinum catalysts had been subsequently invented attempting to address this problem. For example, platinum-cyclovinylmethylsiloxane complex was made immediately after the invention of the Karstedt catalyst (U.S. Pat. No. 3,814,730), and this catalyst is purported to provide longer production process pot life for a vinyl/hydride reactive coating solution mixture. Platinum tetramethyldivinylsiloxane dimethyl maleate and platinum tetramethyldivinylsiloxane dimethyl fumarate were disclosed in the mid-1990's, both of which are claimed to provide longer production process pot life for vinyl/hydride coating solution mixtures. Each of those catalysts is still commonly used in the silicone coating industry.

In order to be useful on medical devices such as surgical needles, it is critical that lubricious silicone coatings be durable and easy to apply in a uniform, consistent manner. A surgical procedure in which tissue is approximated or closed with surgical sutures typically requires multiple passes of the surgical needle and suture through tissue. Ease of penetration over multiple passes through tissue will make the surgeon's job easier and this will likely result in a better tissue repair or closure. The patient will benefit not only by enhanced healing and superior outcome, but also by a faster procedure resulting in a shorter time for possible exposure of the wound or opening to pathogens in the environment, and also requiring a shorter period of time that the patient is under general anesthesia, when anesthesia is required.

Surgical needles are typically manufactured in high speed production processes. For example, U.S. Pat. No. 5,776,268, incorporated by reference, discloses such processes. After the needles are formed and shaped (typically from wire stock), the in-process needles are cleaned, and the needles are coated with lubricious coatings in a conventional manner such as by dipping, spraying, brushing, etc. After application of the coatings in a uniform manner to substantially coat the exterior surfaces of the needles, the needles are then moved into appropriate curing equipment, such as an oven, for a coating curing process wherein energy (e.g., thermal) is provided to cure the silicone coatings.

Silicone coatings are typically prepared at the manufacturing site by mixing the silicone polymer components with a suitable catalyst and solvents. Such coatings and catalysts, especially when of medical grade for use on medical devices, are expensive and typically have what is conventionally known in this art as a short "pot life". The term pot life, as conventionally used in the art, has the meaning that the silicone coatings when mixed with catalyst and ready for application in a coating process typically have a limited amount of time in which they are useful because of cross-linking that occurs at ambient conditions in the production facility. Such short pot life can result in a number of known problems, including for example, premature curing, leading to a viscosity increment of the coating solution during the time of its usage. This will typically cause inconsistencies in the resulting coating on the surface of the medical device, resulting in both visual and performance deficiencies.

There is a need in this art for improved silicone coatings for medical devices that have improved lubricity and durability for multiple passes through tissue. There is also a need for improved silicone coatings that have improved cure times without sacrificing lubricity and durability, and which do not contain potentially harmful ingredients.

There is a further need in the art for improved catalysts for silicone coatings that provide for rapid curing when exposed to heat but which are relatively stable in a silicone coating solution over time at ambient conditions and for extended periods of time in typical production environments.

SUMMARY OF THE INVENTION

Accordingly, novel lubricious silicone coating compositions are disclosed. The coating compositions contain a first cross-linkable silicone polymer having reactive functionalities, a siloxane cross-linking agent, and a second non-cross-linkable silicone polymer. The second non-cross-linkable silicone polymer has a weight average molecular weight greater than about 200,000, preferably about 260,000 to about 10,000,000. The coating compositions may also contain a platinum catalyst.

Another aspect of the present invention is a medical device having a surface, wherein at least part of the surface is coated with the above-described novel silicone coating composition.

Yet another aspect of the present invention is a method of coating a medical device with a silicone, lubricious coating composition. In the novel method of coating the medical device, a medical device is provided having a surface. A lubricious silicone coating is applied to at least part of the surface. The coating composition contains a cross-linkable silicone polymer and a non-cross-linkable silicone polymer, wherein the polymer has a weight average molecular weight greater than about 200,000, preferably about 200,000 to about 10,000,000. The coating also contains a silicone cross-linking agent and a catalyst.

Still yet another aspect of the present invention is a novel platinum catalyst for use with cross-likable silicone coatings. The catalyst consists of a platinum complex having the following formula:

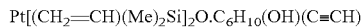

Pt[(CH$_2$=CH)(Me)$_2$Si]$_2$O·C$_6$H$_{10}$(OH)(C≡CH)

A further aspect of the present invention is a method of curing a cross-linkable silicone polymer containing coating solution using the above-described catalyst.

These and other aspects and advantages of the present invention will become more apparent from the following description.

DETAILED DESCRIPTION OF THE INVENTION

The terms silicone and siloxane are conventionally used interchangeably in this art, and that usage has been adopted herein Lubricious Coating Composition The present invention is directed to novel lubricious silicone coating compositions which are particularly useful for coating surfaces of medical devices such as surgical needles and other tissue piercing or cutting devices. The compositions include a mixture of a cross-linkable siloxane polymer and a non-cross-linkable siloxane polymer, a conventional silicone cross-linking agent, and a platinum catalyst. The silicone polymer components are blended with conventional aromatic organic solvents, including, for example, xylene and aliphatic organic solvents (such as, for example, hexane or its commercial derivatives) to form coating solutions or compositions.

The cross-linkable siloxane polymers useful in the coating compositions of the present invention will have reactive functionalities or terminal functional groups, including but not limited to vinyl terminated, hydroxyl and acrylate functional groups. The cross-linkable siloxane polymers that can be used in the lubricious coatings of the present invention preferably include vinyl terminated polydialkylsiloxane or vinyl terminated polyalkoarylsiloxane. Examples include but are not limited to the following vinyl terminated siloxane polymers: polydimethyl siloxane, polydiphenylsilane-dimethylsiloxane copolymer, polyphenylmethylsiloxane, polyfluoropropylmethyl-dimethylsiloxane copolymer and polydiethylsiloxane. It is particularly preferred to use vinyl terminated cross-linkable polymethyl siloxane.

The non-cross-linkable siloxanes that can be used in the practice of the present invention include polydimethyl siloxane, polyalkylmethylsiloxane, such as polydiethylsiloxane, polyfluoropropylmethylsiloxane, polyoctylmethylsiloxane, polytetradecylmethylsiloxane, polyoctadecylmethylsiloxane, and polyalkylmethyl dimethylsiloxane, such as polyhexadecymethylsiloxane-dimethyl siloxane. It is particularly preferred to use non-cross-linkable polymethyl siloxanes with weight average molecular weights (Mw) greater than 200,000, preferably about 200,000 to about 1,000,000, which are in the form of non-flowable gum having a viscosity greater than 600,000 cps.

The cross-linking agents that can be used in the coatings of the present invention include conventional silicone cross-linking agents such as, for example, polymethylhydro siloxane, polymethylhydro-co-polydimethylsiloxane, polyethyhydrosiloxane, polymethylhydrosiloxane-co-octylmethylsiloxane, polymethylhydrosiloxane-co-methylphenylsiloxane. One preferred conventional catalyst for use in the coatings of the present invention is polymethylhydro siloxane. Precise control of cross-link density in the coatings of the present invention is achieved by precise control of the ratio of non-cross-linkable silicone polymer (e.g., polydimethylsiloxane) to fully cross-linked polymer. The fully cross-linked polymer is formed by a reaction between the functionalized cross-linkable polymer and the cross-linking agent, for example, a vinylsilylation reaction between vinyl-terminated polydimethylsiloxane and polymethylhydrosiloxane optionally in the presence of a platinum complex catalyst. The ratio between non-cross-linkable polymer, e.g., polydimethylsiloxane, and fully cross-linked polymer is sufficiently effective to provide structural reinforcement to the resulting interpenetrating polymer networks, and is typically between about 0.1 wt./wt. and about 9 wt./wt., preferably between about 0.43 wt./wt. and about 2.33 wt./wt. The vinyl-terminated cross-linkable base polymer, e.g., polydimethylsiloxane base polymer, useful in the coatings of the present invention will have a weight average molecular weight (Mw) of between about 10,000 and about 500,000 and preferably between about 50,000 to about 250,000. Examples of this polymer include, but are not limited to: Gelest Product Code No. DMS-V51, DMS-V52, DMS-V61, DMS-V71, etc., available from Gelest, Inc., Morrisville, Pa. 19067. The typical molecular structure of vinyl terminated polydimethyldisiloxane is the following:

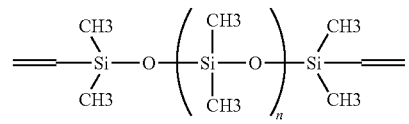

wherein n is defined by the molecular weight.

The cross-linkable siloxane polymer forms the matrix phase of the coating on surface or surfaces of a medical device. Vinyl terminated polydimethylsiloxane reacts with polymethylhydrosiloxane cross-linker in the presence of platinum catalyst under appropriate conditions; the vinyl terminated polydimethylsiloxane linear polymers are fully cross-linked to each other as the result of this reaction. The amount of polymethylhydrosiloxane cross-linker is in large stoichiometric excess compared to vinyl terminated polydimethylsiloxane base polymer. It is believed that the extra SiH functions in the cross-linker react with the OH functions on the surface of the oxide layer of the medical devices, e.g., steel needles, to form Si—O—Fe bonds at elevated temperature. Covalent bonds thus created between the silicone coating and the device or needle surface, as the result of this reaction, result in the adhesive attachment of the coating to the metallic surface.

The polymethyhydrosiloxane cross-linkers, or cross-linking agents, used in the practice of the present invention will have a weight average molecular weight (Mw) between about 1000 and about 3000, and preferably between about 1400 and about 2100. An example of this polymer cross-linker includes, but is not limited to, Gelest Product Code No. HMS-991, HMS-992, available from Gelest, Inc., Morrisville, Pa. 19607. The typical molecular structure of the polymethyhydrosiloxane cross-linker is the following:

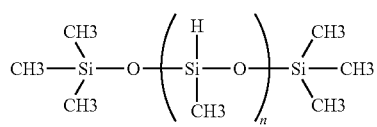

wherein n is defined by the molecular weight.

Polymethylhydro-co-polydimethylsiloxane can also be used as cross-linker or cross-linking agent in the novel coatings of the present invention. Examples of this polymer include, but are not limited to, Gelest Product Code No. HMS-301, HMS-501. The weight average molecular weight of this siloxane polymer cross-linking agent will typically be between about 900 and about 5,000, and preferably about 1,200 to about 3,000. The typical molecular structure of polymethylhydro-co-polydimethylsiloxane cross linker is the following:

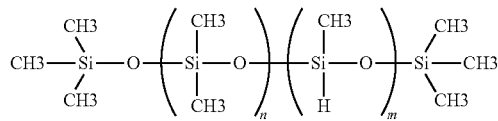

wherein n and m are defined by the molecular weight.

The non-cross-linkable siloxane polymer used in the lubricious coatings of the present invention is preferably trimethylsilyl-terminated polydimethylsiloxane; which is a linear high molecular weight polydimethylsiloxane polymer, and which does not contain reactive functional groups. This polymer provides a non-cross-linked phase in the resulting silicone coating, and is believed to disperse in the matrix phase made from the cross-linked cross-linkable siloxane. The weight average molecular weight of this polymer will typically be greater than about 200,000, preferably between about 200,000 to about 10,000,000, and more preferably between about 400,000 to about 700,000. Examples of this polymer include, but are not limited to, Gelest Product Code No. DMS-D-56, DMS-T62, DMS-T61, DMS-D72. The typical molecular structure of the non-cross-linkable siloxane polymer is illustrated below:

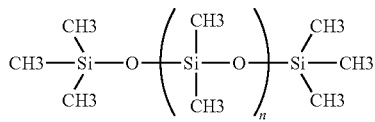

wherein n is defined by the molecular weight.

Catalyst

Bruce Karstedt of GE Silicone invented a highly active platinum catalyst (the "Karstedt catalyst") at the beginning of the 1970's (U.S. Pat. No. 3,775,452). Vinyl-terminated polydimethylsiloxane can react with a polymethylhydrosiloxane cross-linker in less than one minute at ambient temperature with as little as 10 ppm of the Karstedt catalyst. It is typically difficult or impossible to use this catalyst in conventional needle production manufacturing processes because of its high rate of catalytic activity, and since the economics of conventional production processes ideally and typically require up to a one week pot life for the fully catalyzed silicone coating solution. The novel fast curing platinum catalyst of the present invention has been developed to address this issue, and the resulting mixtures of this novel catalyst together with the cross-linkable and non-cross-linkable silicone polymers of the present invention, e.g., vinyl-terminated polydimethylsiloxane and polymethylhydrosiloxane, can be stable at ambient temperatures for more than one week. The cross-linking reaction between the crosslinkable silicone polymer and the cross-linking agent, for example, vinyl-terminated polydimethylsiloxane and polymethylhydrosiloxane, in the presence of the novel catalyst of the present invention can be switched on in less than 10 seconds at elevated temperature. The novel catalyst of the present invention is prepared by reacting the Karstedt catalyst with ethynylcyclohexanol according to Scheme 1 as seen below. The novel catalyst of the present invention provides greater control over curing of the silicone coating solutions. This is conventionally referred to as "command cure".

Scheme 1

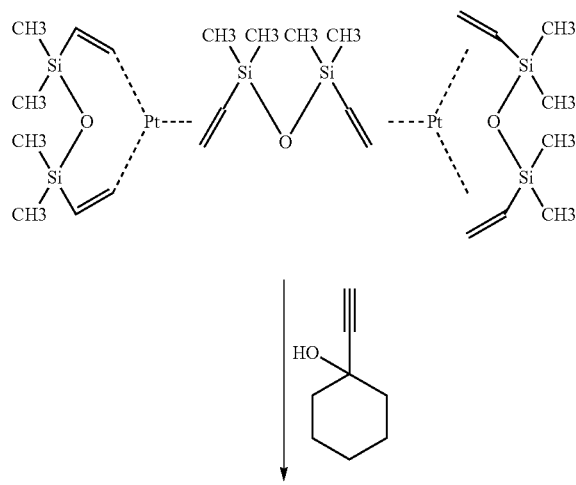

-continued

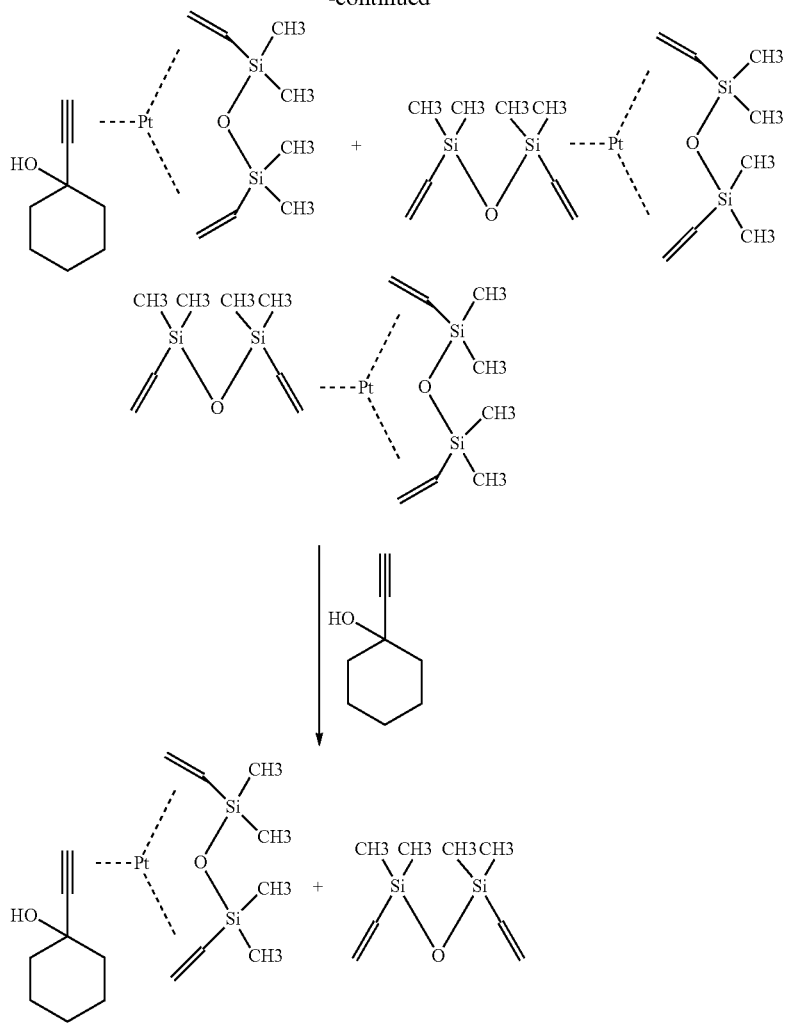

The novel catalyst of the present invention may be prepared in the following manner. Karstedt catalyst in xylene solution is mixed with a low concentration of ethynylcyclohexanol in xylene solution at ambient temperature for a sufficiently effective time to complete the reaction, e.g., a half an hour, and completion of the reaction is indicated by a change of the color of the reaction mixture, from clear to light brown. The resulting catalyst solution containing the novel catalyst of the present invention is ready to use in the preparation of the lubricious coating solutions of the present invention. The formula of the resulting platinum complex catalyst (platinum divinyltetramethyldisiloxane complex) is:

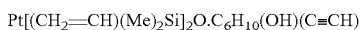
Pt[(CH$_2$=CH)(Me)$_2$Si]$_2$O.C$_6$H$_{10}$(OH)(C≡CH)

It should be noted that the resulting catalyst reaction mixture will contain a small amount of the reaction product divinyltetramethyldisiloxane. This component does not affect the catalyst, and is a low boiling point component that is rapidly boiled off. Accordingly, purification of the catalyst mixture to remove divinyltetramethyldisiloxane is optional, and it is believe that its presence will not affect the cross-linking reaction of a cross-linkable silicone polymer. The novel catalyst of the present invention is inhibited at low or ambient temperatures and activated at higher or curing temperatures, that is, the catalyst is inactivated at lower or ambient temperatures and activated at higher or curing temperatures. This allows for command cure (command cure catalytic action) of the cross-linkable components in silicone coatings to rapidly form coating films at desired curing temperatures, and provides for long pot life.

Although the novel catalyst of the present invention is preferred and most desirable in the coating compositions of the present invention, it is also possible to use conventional catalysts with these coating compositions. The conventional catalysts include platinum-cyclovinylmethylsiloxane complex (Ashby Karstedt Catalyst), platinum carbonyl cyclovinylmethylsiloxane complex (Ossko catalyst), platinum divinyltetramethyldisiloxane dimethyl fumarate complex, platinum divinyltetramethyldisiloxane dimethyl maleate complex and the like and equivalents.

Solvent and Coating Mixing Procedure

The above-described silicone polymers and platinum catalysts, including the novel platinum complex catalyst of the present invention, are dispersed into organic solvents to form the novel lubricious coating solutions or compositions of the present invention. Both aromatic and aliphatic solvents can be used for the silicone dispersions, however, aromatic solvents are most commonly used for silicone dispersions. Typical examples of useful aromatic solvents include, but are not limited to, xylene and toluene. Aliphatic solvents which are useful include, but are not limited to, pentane, heptanes, hexane and their mixtures. An example of an aliphatic solvent mixture is Exxon Isopar K solvent. The organic solvents are added at a concentration sufficient to provide effective blending of the silicone polymer components into a homogeneous coating solution. The total solvent concentration sufficient to be effective is typically between about 75 wt. % to about 99.5%, and is more typically between about 85 wt. % to about 98.5 wt. %, depending upon the coating thickness requirement. Those skilled in the art will appreciate that the coating thickness can be engineered by changing the solids content of the coating solution.

The following procedure as described utilizes conventional mixing equipment in typical production facilities. The coating compositions of the present invention may be preferably prepared in the following manner. Initially, a suitable organic solvent such as xylene is added to a conventional mixing vessel together with a platinum catalyst and mixed for a sufficiently effective time, for example, up to about 10 minutes to form a solution. Then, a non-cross-linkable silicone polymer component such as trimethylsilyl-terminated polydimethylsiloxane and vinyl-terminated cross-linkable silicone polymer component such as polydimethylsiloxane are dispersed into the solution for a sufficiently effective time; for example, for up to about two hours until fully homogeneous. A suitable organic solvent such as Isopar K solvent is then added to the solution, and the solution is further mixed for a sufficiently effective time, for example, for about one hour prior to the addition of a cross-linking agent such as polymethylhydrosiloxane cross-linker. Then, the cross-linking agent is added to the solution and the solution is fully blended for a sufficiently effective time. The length of such time can be, for example, one additional hour after all of the components have been added to the mixing vessel.

Other conventional blending and mixing processes and equipment may be used to manufacture the novel silicone coating compositions of the present invention. For example, the sequence can be modified to some extent when using various other suitably effective conventional mixing equipment, such as a double planetary mixer. All of the components may be mixed in one step in such equipment.

Although not necessarily preferred, in order to reduce VOC emissions, it is possible to formulate the lubricious coating compositions of the present invention in a less volatile organic solvent, an aqueous/organic solvent mixture, or an aqueous solvent solution. This can be done by done in a conventional manner similar to that used for low VOC polymeric coatings.

In the following paragraph the wt. % is the wt. % of total solid content in the coating solution. The novel coating compositions of the present invention will contain sufficient amounts of the polymeric components, cross-linking agent, catalyst, and solvent to effectively provide a silicone coating having high lubricity and durability, a long pot life, and suitable for application in conventional coating processes using conventional coating equipment. Typically, the amount of the non-cross-linkable silicone polymer will be about 10 wt. % to about 90 wt. % (total solids), more typically about 30 wt. % to about 70 wt. % (total solids), and preferably about 40 wt. % to about 60 wt. % (total solids). The amount of the cross-linkable silicone polymer will typically be about 10 wt. % to about 90 wt. % (total solids), more typically about 30 wt. % to about 70 wt. % (total solids), and preferably about 40 wt. % to about 60 wt. % (total solids). The amount of the silicone cross-linking agent will typically be about 0.2 wt. % to about 1.8 wt. % (total solids), more typically about 0.6 wt. % to about 1.4 wt. % (total solids), and preferably about 0.8 wt. % to about 1.2 wt. % (total solids). The amount of the platinum catalyst based upon the total solids in the novel lubricious silicone coating compositions (platinum element in total solids) of the present invention will typically be about 0.0004 wt. % to about 0.0036 wt. %, more typically about 0.0012 wt. % to about 0.0028 wt. %, and preferably about 0.0016 wt. % to about 0.0024 wt. %.

The amount of organic solvent in the coating compositions of the present invention will typically be about 75 wt. % to about 99.5 wt. %, more typically about 28 wt. % to about 99 wt. %, and preferably about 15 wt. % to about 98.5 wt. %. Those skilled in the art will appreciate that the amount of solvent present in the novel coating compositions of the present invention will vary with several factors, and that the solvent quantity in the coating compositions will be selected to engineer an efficacious coating. The factors typically considered include the method of application, the method of cure, the coating equipment utilized, ambient conditions, thickness, etc. It will be appreciated that each of the components of the coating compositions of the present invention may consist of blends of those components. For example, two or more different molecular weight non-cross-linkable silicone polymers may be used, or two or more cross-linkable silicone polymers having different functionalities and/or molecular weights may be used, etc.

Coating Process

The novel silicone lubricious coating compositions of the present invention are applied to one or more surfaces of a medical device, such as a surgical needle, using conventional coating techniques and processes and conventional coating equipment. One example of coating equipment that can be used to apply the coatings includes, but is not limited to, simple dip coating tanks and in-line convection ovens for curing. The coating compositions can also be applied by conventional brushing, rolling, or spraying processes, and any equivalent processes. The vinyl silylation addition cross-linking reaction can be completed (i.e., the coating can be cured) in-line by passing the coated device through a drying oven for a sufficiently effective time. The curing times will vary, for example, from about 5 seconds to about one hour, and will vary with respect to parameters such as the cross-linker concentration, catalyst concentration, coating thickness, ambient conditions, device construction and material type, etc. However, the cure times can be as short as about 20 seconds at 450° C., or about 6 seconds at 600° C. Flash cure (i.e., instantaneous or rapid cure) can also be achieved with the present lubricious silicone coating containing the novel catalyst of the present invention. Other conventional curing techniques which can be utilized with the novel silicone coating compositions of the present invention include thermal (e.g., convection heating), ultraviolet light, plasma, microwave radiation, electromagnetic coupling, ionizing radiation, laser, and the like. Prior to coating, the surfaces of the medical devices will be prepared in a conventional manner using conventional processes such as electro-polishing, oxidation, ultrasonic cleaning, plasma etch, chemical cleaning, and the like.

Test Procedures for Coating Performance

Coating performance for medical devices coated with the novel compositions of the present invention can be tested with a variety of conventional friction or adhesion tests. In the case of surgical needles, coating performance, durability and integrity are evaluated using a conventional needle penetration testing apparatus. A coated surgical needle is held using a mounting fixture on the apparatus, such as self-locking tweezers or a similar holding device. The coated needle is then passed through a polymeric medium by the apparatus; the polymeric medium is selected to be representative of general human tissue. Typically, approximately half of the needle length is passed through the medium and then retracted prior to the next pass. The test media may be a type of synthetic rubber (e.g., Duraflex™, manufactured by Monmouth Rubber and Plastic Corporation, Monmouth, N.J.). The needle can be passed through the penetratable material typically for about one to about twenty times, more typically between about one to about twenty-five times, and most preferably between about one to about thirty times. The needle is then retracted from the media. The maximum force is recorded for each pass and is used as a measure of the coating performance. Various attributes of coating performance can be tested using these techniques, including durability and lubricity.

A typical test includes using 10 needles that are individually passed through the media 30 times each. The maximum force is recorded for each pass and used as a measure of the coating performance. Typically the penetration force increases with each successive pass as the coating wears off from the needle.

As mentioned previously above, the medical devices that may be coated with the novel lubricious coatings include conventional medical devices such as surgical needles, hypodermic needles, catheters, surgical probes, endoscopes, syringes, scalpels, cutting blades, orthopaedic implants, trocars, cannulas, and the like. The medical devices will be constructed from conventional biocompatible materials including surgical stainless steels, PTFE, glass, alloyed steels, refractory metal alloys, memory alloys, polymers, composites comprising metallic and non-metallic components ingredients, combinations thereof, and the like. The biocompatible materials may include nonabsorbable materials and bioaborbable materials.

The following examples are illustrative of the principles and practice of the present invention, although not limited thereto:

Example 1

Platinum Catalyst Synthesis Procedure

A novel platinum complex catalyst of the present invention was made in the following manner. 60 grams of 1 wt. % Gelest SIP 6831 (2.2 wt. % platinum divinyl tetramethyldisiloxane complex, Karstedt catalyst) xylene were mixed with 60 grams of 1 wt. % ethynylcyclohexanol xylene solution in a suitable mixing vessel for about 30 minutes at ambient temperature until the mixture color changed to a light brown color. This catalyst solution is referred to as Catalyst Formulation 1, and the platinum complex catalyst (platinum divinyltetramethyldisiloxane complex) has the formula:

$$Pt[(CH_2=CH)(Me)_2Si]_2O \cdot C_6H_{10}(OH)(C\equiv CH)$$

Example 2

Viscosity Measurements on FullyCatalyzed Silicone Solution Reactivity/Stability Test A pot life study was conducted using a silicone polymer coating composition formulation as described below and outlined in Table 1. Three different catalysts were used in three different variations of the formulation, including the novel catalyst of Example 1 (Catalyst Formulation 1), to investigate the effect of the catalyst upon the pot life of the coating composition.

TABLE 1

Silicone Polymer Coating Formulation 2 for Pot Life Studies

| Component | Trade Name/Description | Weight (g) |
|---|---|---|
| Trimethylsilyl terminated poly dimethyl siloxane | Gelest DMS T72 | 300 |
| Dimethylvinyl silyl terminated poly dimethyl siloxane | Gelest DMS V52 | 300 |
| 0.01% Platinum catalyst solution | | 120 |
| Trimethylsilyl terminated polymethylhydrosiloxane | Gelest DMS HMS 991 | 6 |
| Solvent | Xylene | 1274 |

The viscosity of the formulations was measured over a period of time and the results are summarized in Table 2. The viscosity measurement results of the formulations using conventional catalysts (Ashby and Karstedt, 0.01% solution) were also included in this table for the purpose of comparison.

TABLE 2

Viscosity of Full Catalyzed Silicone Solutions, Using Different Catalysts

| Catalyst Time | (Catalyst Formulation 1) | Ashby | Karstedt |
|---|---|---|---|
| 0 min* | 4630 | 4630 | 4630 |
| 5 min | 4827 | 5040 | gel |
| 30 min | 4840 | 6253 | |
| 1 hr | 4840 | 10707 | |
| 2 hr | 4910 | gel | |
| 1 day | 4920 | | |
| 2 day | 4960 | | |
| 6 day | 5050 | | |
| 12 day | 5110 | | |
| 23 day | 5310 | | |
| 28 day | 5360 | | |
| 40 day | 5460 | | |
| 56 day | 5470 | | |

*Measured on the solution without platinum catalyst

The Karstedt catalyst gave less than 2 minutes pot life and the silicone solution containing the Ashby catalyst gelled in less than 2 hours at ambient temperature. The formulation containing the catalyst of Example 1 (Catalyst Formulation 1) gave less than a 5% change in viscosity after 6 days and increased only 11% by the 28$^{th}$ day. The viscosity difference was minor and within the specification for typical silicone coating solutions.

Example 3

Molecular Weight Study of Non-Cross Linkable Silicone Component: Summary of Formulations Uncoated Ethicon BV-175 surgical needles (8 mil diameter, no suture attached, Ethicon, Inc., Somerville, N.J.) were coated with lubricious silicone coating compositions. In the first set of experiments, the concentration of the cross-linkable vinyl terminated polydimethylsiloxane, polymethylhydrosiloxane cross-linker, catalyst and solvent were fixed, a series of non-crosslinkable trimethylsilyl terminated polydimethylsiloxanes with different weight average molecular weights were used at the same concentration for this evaluation to study the effect of molecular weight of the non-cross linkable component. The details of these trimethylsilyl terminated polydimethylsiloxanes are summarized in table 3-1.

TABLE 3-1

Summary of Different Grades of Trimethylsilyl Terminated Polydimethylsiloxanes purchased from Gelest Inc.

| Gelest Trade Name | Viscosity (cSt) | Molecular Weight (Mw) |
|---|---|---|
| DMS-T51 | 100,000 | 139,000 |
| DMS-T53 | 300,000 | 204,000 |
| DMS-T56 | 600,000 | 260,000 |
| DMS-T61 | 1,000,000 | 308,000 |
| DMS-T63 | 2,500,000 | 423,000 |
| DMS-T72 | 20,000,000 | >500,000 |

Formulation 3A used Gelest DMS-T51 as non-cross linkable component and its details are summarized in table 3-2.

TABLE 3-2

Formulation 3A

| Component | Trade Name | Weight (g) |
|---|---|---|
| Trimethylsilyl terminated polydimethylsiloxane | Gelest DMS-T51 | 1144 |
| Dimethylvinyl silyl terminated polydimethylsiloxane | Gelest DMS-V52 | 1144 |
| Catalyst solution as per Example 1 | | 457.6 |
| Trimethylsilyl terminated polymethylhydrosiloxane | Gelest DMS HMS-991 | 22.9 |
| Solvent 1 | Xylene | 5087.4 |
| Solvent 2 | Exxon Isopar K | 8144 |

Formulation 3B used Gelest DMS-T53 as the non-cross linkable component and its details are summarized in Table 3-3.

TABLE 3-3

Formulation 3B

| Component | Trade Name | Weight (g) |
|---|---|---|
| Trimethylsilyl terminated polydimethylsiloxane | Gelest DMS-T53 | 1144 |
| Dimethylvinyl silyl terminated polydimethylsiloxane | Gelest DMS-V52 | 1144 |
| Catalyst solution as per Example 1 | | 457.6 |
| Trimethylsilyl terminated polymethylhydrosiloxane | Gelest DMS HMS-991 | 22.9 |
| Solvent 1 | Xylene | 5087.4 |
| Solvent 2 | Exxon Isopar K | 8144 |

Formulation 3C used Gelest DMS-T56 as the non-cross linkable component and its details are summarized in table 3-4.

TABLE 3-4

Formulation 3C

| Component | Trade Name | Weight (g) |
|---|---|---|
| Trimethylsilyl terminated polydimethylsiloxane | Gelest DMS-T56 | 1144 |
| dimethylvinyl silyl terminated polydimethylsiloxane | Gelest DMS-V52 | 1144 |
| Catalyst solution as per Example 1 | | 457.6 |
| Trimethylsilyl terminated polymethylhydrosiloxane | Gelest DMS HMS-991 | 22.9 |
| Solvent 1 | Xylene | 5087.4 |
| Solvent 2 | Exxon Isopar K | 8144 |

Formulation 3D used Gelest DMS-T61 as the non-cross linkable component and its details are summarized in table 3-5.

TABLE 3-5

Formulation 3D

| Component | Trade Name | Weight (g) |
|---|---|---|
| Trimethylsilyl terminated polydimethylsiloxane | Gelest DMS-T61 | 1144 |
| dimethylvinyl silyl terminated polydimethylsiloxane | Gelest DMS-V52 | 1144 |
| Catalyst solution as per Example 1 | | 457.6 |
| Trimethylsilyl terminated polymethylhydrosiloxane | Gelest DMS HMS-991 | 22.9 |
| Solvent 1 | Xylene | 5087.4 |
| Solvent 2 | ExxonIsopar K | 8144 |

Formulation 3E used Gelest DMS-T63 as the non-cross linkable component and its details are summarized in table 3-6.

TABLE 3-6

Formulation 3E

| Component | Trade Name | Weight (g) |
|---|---|---|
| Trimethylsilyl terminated polydimethylsiloxane | Gelest DMS-T63 | 1144 |
| dimethylvinyl silyl terminated polydimethylsiloxane | Gelest DMS-V52 | 1144 |
| Catalyst solution as per Example 1 | | 457.6 |
| Trimethylsilyl terminated polymethylhydrosiloxane | Gelest DMS HMS-991 | 22.9 |
| Solvent 1 | Xylene | 5087.4 |
| Solvent 2 | Exxon Isopar K | 8144 |

Formulation 3F used Gelest DMS-T72 as the non-cross linkable component and its details are summarized in table 3-7.

TABLE 3-7

Formulation 3F

| Component | Trade Name | Weight (g) |
|---|---|---|
| Trimethylsilyl terminated polydimethylsiloxane | Gelest DMS-T72 | 1144 |

TABLE 3-7-continued

Formulation 3F

| Component | Trade Name | Weight (g) |
|---|---|---|
| Dimethylvinyl silyl terminated polydimethylsiloxane | Gelest DMS-V52 | 1144 |
| Catalyst solution as per Example 1 | | 457.6 |
| Trimethylsilyl terminated polymethylhydrosiloxane | Gelest DMS HMS-991 | 22.9 |
| Solvent 1 | Xylene | 5087.4 |
| Solvent 2 | Exxon Isopar K | 8144 |

Formulation 3G was identical to Formulation 3F except for the type of catalyst used in the formulation and its details are summarized in table 3-8.

TABLE 3-8

Formulation 3G

| Component | Trade Name | Weight (g) |
|---|---|---|
| Trimethylsilyl terminated polydimethylsiloxane | Gelest DMS-T72 | 1144 |
| dimethylvinyl silyl terminated polydimethylsiloxane | Gelest DMS-V52 | 1144 |
| 0.02% Ashby catalyst | 0.05% Gelest SIP 6832-2 in xylene | 457.6 |
| Trimethylsilyl terminated polymethylhydrosiloxane | Gelest DMS HMS-991 | 22.9 |
| Solvent 1 | Xylene | 5087.4 |
| Solvent 2 | Exxon Isopar K | 8144 |

Formulation 3H was also prepared with higher loading of organic solvent Isopar K for a two layer coating study and the details are summarized in Table 3-9

TABLE 3-9

Formulation 3H

| Component | Trade Name | Weight (g) |
|---|---|---|
| Trimethylsilyl terminated polydimethylsiloxane | Gelest DMS T72 | 960 |
| Dimethylvinyl silyl terminated polydimethyl siloxane | Gelest DMS V52 | 960 |
| Catalyst solution per Example 1 | | 384 |
| Trimethylsilyl terminated polymethylhydrosiloxane | Gelest DMS HMS 991 | 19.2 |
| Solvent 1 | Xylene | 4269.1 |
| Solvent 2 | Exxon Isopar K | 9408 |

Example 4

Molecular Weight Study of Non-Cross-linkable Silicone Components: Performance Evaluations Uncoated BV175 needles (Ethicon, Inc.) were dipped into the coating solutions of Formulations 3A-3G by hand and the excess silicone coatings were removed by compressed air. The coated needles were heated in a conventional convection oven at 195° C. for 30 minutes Coating performance for medical devices coated with the novel compositions of the present invention can be tested with a variety of conventional friction or adhesion tests. In the case of surgical needles for this Example 4, coating performance, durability and integrity were evaluated using a conventional needle penetration testing device. Each coated surgical needle was mounted and held in a mounting fixture on the apparatus such as g self-locking tweezers or a similar holding device.

The coated needle was then passed by the apparatus through a polymeric medium that was selected to be representative of general human tissue. Approximately half of the needle length was passed through the medium and then retracted prior to the next pass. The test media used for this example was a type of synthetic rubber (Duraflex™, Manufacture by Monmouth Rubber and Plastic Corporation, Monmouth, N.J.). Each test included using 10 needles that were individually passed through the media 30 times each. The maximum force was recorded for each pass and used as a measure of the coating performance. Typically the penetration force increases with each successive pass as the coating wears off from the needle.

Formulation 3A to 3F are identical to each other apart from the molecular weight of the non-cross linkable silicone. The average penetration force for the $1^{st}$, $10^{th}$, $20^{th}$ and $30^{th}$ pass of a coated needle for each formulation is summarized in Table 4-1.

TABLE 4-1

Needle Penetration Test: Example 4, (Formulations 3A to 3F, Trimethylsilyl-Terminated Polydimethylsiloxane with Different Molecular Weights)

| | Penetration Force (g) | | | |
|---|---|---|---|---|
| Formulation | 1st | 10th | 20th | 30th |
| 3A | 29 | 54 | 65 | 70 |
| 3B | 23 | 41 | 50 | 55 |
| 3C | 22 | 33 | 41 | 45 |
| 3D | 21 | 31 | 38 | 42 |
| 3E | 20 | 30 | 36 | 39 |
| 3F | 18 | 27 | 32 | 35 |

The needle penetration test results showed that lower molecular weight trimethylsilyl-terminated polydimethylsiloxane (<200,000) gave comparatively poor lubrication performance with substantially higher penetration force required for insertion into the test media.

Needle penetration test results showed that conventional catalysts gave comparable lubrication performance when used in the novel coatings of the present invention compared to the novel catalyst of the present invention (Example 1) with similar penetration force required for insertion into the test media, as illustrated in Table 4-2.

TABLE 4-2

Needle Penetration Test: Example 4, (Formulation 3F and 3G, with Different Platinum Catalyst)

| | Penetration Force (g) | | | |
|---|---|---|---|---|
| Formulation | 1st | 10th | 20th | 30th |
| 3F | 18 | 27 | 32 | 35 |
| 3G | 20 | 27 | 30 | 31 |

Example 5

Coating Process Optimization, Cure Time Study on the Best Formula

Uncoated BV175 needles (Ethicon, Inc.) were dipped into the coating composition of Formulation 3F by hand and any excess silicone coating composition was removed by compressed air. The coated needles were heated at 195° C. for one minute prior to the application of a second layer of coating, using Formulation 3H, applied in a similar manner. The coated needles were divided into three sets and then cured at 195° C. for 2 minutes, 30 minutes and 7 hours, respectively, in a conventional convection oven to provide three sets of cured needles having three different cure times, with the needles having two layers of coating. Penetration testing was performed on these three sets of needles as described in Example 4. The results are from penetration testing done using 8 individual needles. The coated needles were penetrated into the test media 30 times each. The average penetration force for each pass is summarized in Table 5.

TABLE 5

Needle Penetration Test: Example 5
(Cure at Different Time Periods)

| Penetration# | Avg. Force (g) 2 minute cure | Avg. Force (g) 30 minute cure | Avg. Force (g) 7 hr. cure |
|---|---|---|---|
| 1 | 16 +/− 1 | 16 +/− 1 | 18 +/− 2 |
| 10 | 21 +/− 1 | 21 +/− 1 | 22 +/− 2 |
| 20 | 23 +/− 1 | 22 +/− 2 | 24 +/− 1 |
| 30 | 24 +/− 1 | 24 +/− 3 | 25 +/− 1 |

Only minor differences were observed on the coated BV175 needles having two layers of coating cured for different lengths of time. This indicates the robustness of the coatings of the current invention, wherein a wide range of curing times resulted in almost identical performance. Coatings known in the art typically demonstrate significant performance variability depending upon the curing time.

Example 6

Production Run in Production Facility

Uncoated BV175 needles (Ethicon, Inc.) were coated with the coating composition of Formulation 3F via a conventional dipping process and then flash dried at 250° C. in a conventional furnace or oven for approximately 20 seconds and taken up on a spool. The spool of needles was then exposed to a temperature of 195° C. for 30 minutes. Penetration testing was performed as described in the previous Examples. The results are for penetration testing done using 10 individual needles. The coated needles were penetrated 20 times each.

The average penetration force for each pass is summarized in Table 6. A set of Multipass™ coated Ethicon BV-175 needles was tested as the control sample for the purpose of comparison, and the results are also included in Table 6.

TABLE 6

Needle Penetration Test: Example 6.

| Penetration# | Avg. Force (g) Formulation 3F Coating | Avg. Force (g) Prior Art Coating Mulitpass Coated |
|---|---|---|
| 1 | 15 +/− 3 | 17 +/− 1 |
| 10 | 23 +/− 3 | 30 +/− 2 |
| 20 | 27 +/− 3 | 35 +/− 3 |

As seen in Table 6, the needles coated with the novel coating compositions of the present invention (e.g., coated with the coating solution of Formulation 3F), which contain both cross-linked and non-cross linked polydimethylsiloxane polymer, produced a coating that is more durable than the needles coated with a prior art silicone coating composition. The average force of the 10th penetration of the needle with the coating of Example 3 (Formulation 3F) was seen to be 23.3% less than the control coated needle; and the average of the 20th penetrations was 22.9% less. The structural formation of the new coatings (Formulation 3F) typically took less than 2 minutes. A cure time of 30 minutes was used for Example 4 and Example 6 to ensure the removal of organic solvents, which is significantly less than the cure time required for the formation of the control coating (4 hr. at temperature of 195° C.).

The novel coatings and catalyst of the present invention have many advantages compared with the coatings and catalysts of the prior art. The coatings allow for precise control over the cross-linked polymer network structure, leading to consistency of the resulting coatings and the consistency of the performance of coated devices, in particular coated surgical needles. The coatings provide a unique polymeric network structure, which provides both lubricity and durability of the resulting silicone coating. The catalyst provides command cured catalytic action, enabling the coating solution to form a film rapidly while possessing desirably long pot life. The catalyst is inhibited at low or ambient temperatures and uninhibited or reactivated at higher or curing temperatures. The coatings and catalysts provide for more efficient coating and curing processes.

Although this invention has been shown and described with respect to detailed embodiments thereof, it will be understood by those skilled in the art that various changes in form and detail thereof may be made without departing from the spirit and scope of the claimed invention.

I claim:

1. A catalyst solution for cross-linkable silicone polymer coatings, consisting essentially of platinum divinyltetramethyldisiloxane ethynylcyclohexanol complex in xylene having the formula:

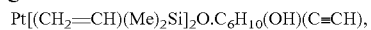

wherein in the combination of said catalyst with a cross linkable siloxane formulation, there is less than a 5% change in viscosity after 6 days at ambient temperature.

2. A catalyst solution for cross-linkable silicone polymer coatings, consisting essentially of platinum divinyltetramethyldisiloxane ethynylcyclohexanol complex as a reaction product of a platinum divinyl tetramethyldisiloxane and an ethynylcyclohexanol in xylene having the formula:

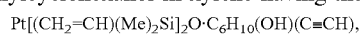

and other reaction products of the platinum divinyl tetramethyldisiloxane and the ethynylcyclohexanol, wherein in the combination of said catalyst with a cross linkable siloxane formulation, there is less than a 5% change in viscosity after 6 days at ambient temperature.

* * * * *